United States Patent [19]
Reed

[11] Patent Number: 5,891,067
[45] Date of Patent: Apr. 6, 1999

[54] WALKING CAST WITH A REMOVABLE SOLE AND METHOD OF MAKING

[76] Inventor: Benjamin David Reed, 217 Virginia Ave. #306, Lexington, Ky. 40508

[21] Appl. No.: 979,173

[22] Filed: Nov. 26, 1997

Related U.S. Application Data

[60] Provisional application No. 60/035,300 Jan. 10, 1997.

[51] Int. Cl.[6] ....................................................... A61F 5/00
[52] U.S. Cl. .................................................. 602/8; 602/10
[58] Field of Search .................................... 602/5, 10, 11, 602/23, 27–29; 36/100, 101, 15, 19.5; 128/882

[56] References Cited

U.S. PATENT DOCUMENTS

| | | |
|---|---|---|
| D. 107,253 | 11/1937 | Pick . |
| D. 262,156 | 12/1981 | Grubelnig . |
| D. 270,001 | 8/1983 | Felton . |
| D. 299,787 | 2/1989 | Bates . |
| D. 311,989 | 11/1990 | Parker et al. . |
| 2,816,541 | 12/1957 | Schultz ........................ 602/27 |
| 3,680,550 | 8/1972 | Tunstall . |
| 3,735,758 | 5/1973 | Novotney . |
| 3,820,254 | 6/1974 | Kopacsi . |
| 4,887,369 | 12/1989 | Bailey et al. . |
| 4,888,225 | 12/1989 | Sandvig et al. ............. 602/11 X |
| 4,926,568 | 5/1990 | Coffman . |
| 4,966,135 | 10/1990 | Renfrew ......................... 602/3 |
| 5,070,630 | 12/1991 | Edmundson . |
| 5,317,822 | 6/1994 | Johnson . |
| 5,433,695 | 7/1995 | Drennan . |
| 5,569,174 | 10/1996 | Varn ............................. 602/27 |
| 5,593,383 | 1/1997 | DeToro ........................ 602/27 |

FOREIGN PATENT DOCUMENTS

| | | |
|---|---|---|
| 673716 | 6/1952 | United Kingdom . |
| WO 86/04489 | 8/1986 | WIPO . |
| WO 89/04125 | 5/1989 | WIPO . |

OTHER PUBLICATIONS

Zimmer, Fracture Appliances, p. 116, Feb. 1, 1947.

*Primary Examiner*—Richard J. Apley
*Assistant Examiner*—Denise Pothier
*Attorney, Agent, or Firm*—Richard C. Litman

[57] ABSTRACT

A removable sole for a walking cast, a walking cast having the removable sole, and a method of making the walking cast and the removable sole. A bandage is permanently bonded to a walking cast, and a sole body is removably attached to the bandage. The bandage has a top surface bonded to the bottom and side surfaces of the cast, and a bottom surface with a strip of hook and loop fastener material. When the cast is plaster, the bandage is preferably adhered to the cast while the plaster is still wet. When a fiberglass cast is used, an adhesive is applied to the top surface of the bandage to bond the bandage to the cast. The sole body has a concave top surface with a complimentary strip of hook and loop fastener material that mates with the hook and loop fastener material on the bandage. The loop fastener material on the bandage also protects the cast and the surface being walked on, when the sole body is removed. A patient can simply peel off the sole body when it is not needed, as when in bed, or to avoid tracking dirt on a carpet that has been picked up by the sole body. To reattach the sole body, the patient simply steps on it with the cast.

14 Claims, 3 Drawing Sheets

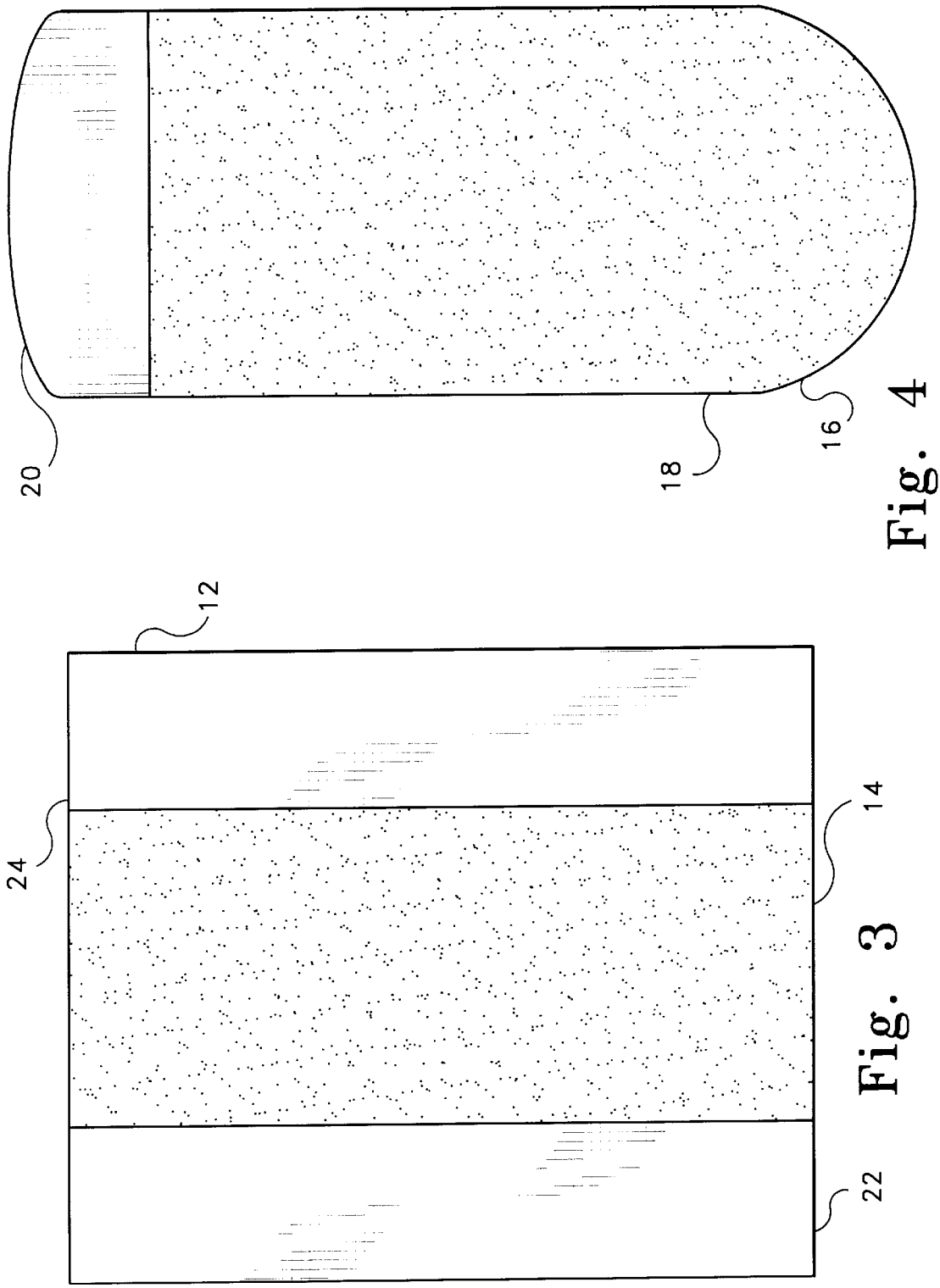

WALKING CAST WITH A REMOVABLE SOLE AND METHOD OF MAKING

CROSS-REFERENCE TO RELATED APPLICATION

This application claims the benefit of U.S. Provisional Patent Application Ser. No. 60/035,300, filed Jan. 10, 1997.

BACKGROUND OF THE INVENTION

1. Field of the Invention

The present invention relates to a removable sole for a walking cast and, more specifically, to an integral bandage on the bottom of a walking cast having loop fasteners that engage hook fasteners on the top of a removable sole. The method of making the walking cast with a removable sole is also disclosed.

2. Description of the Related Art

Four to six weeks after an initial cast is first applied to a broken leg, a doctor removes the original cast and applies a walking cast. Most walking casts include a crude, ill fitting boot or sole, that provides a tread on the bottom of the cast to protect the plaster portion of the cast. The prior art devices tend to be heavy, cumbersome, difficult to remove (or not removable at all), and unattractive. There is, therefore, a need for a more comfortable, lighter, better looking, and easier to use walking cast with a removable sole.

U.S. Design Pat. Nos. Des. 107,253, issued on Nov. 30, 1937, to Oswald M. Pick, Des. 262,156, issued on Dec. 8, 1981, to Alfred Grubelnig, Des. 270,001, issued on Aug. 2, 1983, James R. Felton, Des. 299,787, issued on Feb. 14, 1989, to Norman R. Bates, and Des. 311,989, issued on Nov. 13, 1990, to Mark G. Parker et al. all disclose designs for shoe soles, or walking aids or covers for casts. Functional details of the designs are not disclosed.

U.S. Pat. No. 3,680,550, issued on Aug. 1, 1972, to Don M. Tunstall, discloses a sole for a walking cast, having a base plate embedded in the cast, with a leaf spring to absorb shock when walking. The sole is not removably attached to the cast.

U.S. Pat. No. 3,735,758, issued on May 29, 1973, to Marguerite E. Novotney, discloses a foot and ankle cast enclosure, which surrounds a foot portion of a cast, and has straps with hook and loop (Velcro) fasteners. The enclosure is bulky and difficult to remove.

U.S. Pat. No. 3,820,254, issued on Jun. 28, 1974, to John Kopacsi, discloses a foot cast shoe type cover, having a sock type foot cover of flexible waterproof material, with a sole, a heel accommodating hole, and a rear closure that may include a hook arid loop fastener (Velcro). The device must be put on and removed from the cast like a shoe cover.

U.S. Pat. No. 4,887,369, issued on Dec. 19, 1989, to Angileen Bailey et al., discloses a convertible shoe with separate top and bottom parts that can be attached by snap fasteners. The shoe is not designed for use with a cast.

U.S. Pat. No. 4,926,568, issued on May 22, 1990, to Cynthia L. Coffman, discloses a sole protector with hook fasteners that attach to the bottom of socks (or slippers with fabric bottoms), without the use of loop fasteners. The use of the protector with loop fasteners on a cast is not taught.

U.S. Pat. No. 5,070,630, issued on Dec. 10, 1991, to Ross Edmundson, discloses a decorative cast cover, which is fastened to a cast using hook and loop fasteners, and resembles a shoe in appearance. The bottom of the cast is not covered, and therefore the sole of the cast is not protected.

U.S. Pat. No. 5,317,822, issued on Jun. 7, 1994, to Joshua F. Johnson, discloses an athletic shoe with an interchangeable wear sole. The sole is removably retained by hook and loop type fasteners and resilient knobs that fit into slots. The sole is not designed for use with a cast.

U.S. Pat. No. 5,433,695, issued on Jul. 18, 1995, to Denis B. Drennan, discloses a foot piece of elastomeric material that it is permanently attached to the bottom of a walking cast. The foot piece is not removable.

British Patent Specification No. 673,716, published on Jun. 11, 1952, to Duncan Galbraith Wright, discloses a walking plaster appliance for use by orthopedic patients. The appliance has laces that must be tied and untied to put on and take off the appliance.

International Application No. 86/04489, published on Aug. 14, 1986, to Jack J. Saffron and Mark V. Goodyear, discloses replaceable shoe soles, removably retained on athletic shoes by ridges that fit into grooves. The soles are not designed for use with a cast.

International Application No. 89/04125, published on May 18, 1989, to Karl Birkenstock, discloses a molded inner sole for a shoe or sandal, with a sloping support. The sole is permanently bonded to an outsole, and is not removable.

None of the above inventions and patents, taken either singly or in combination, is seen to describe the instant invention as claimed.

SUMMARY OF THE INVENTION

After a walking cast is applied to a broken leg, an outpatient must handle the difficult task of moving about. While walking, the bottom of the cast can accumulate dirt and debris thereon. In addition, in most cases the bottom surface of the cast does not provide a suitable tread for contacting the ground. To overcome these drawbacks, the present invention provides an easily removed and replaced sole for the bottom of a walking cast.

The main components of the invention include a bandage that is permanently bonded to the cast, and a sole body removably attached to the bandage. The bandage has a top surface that is bonded to the bottom and side surfaces of the cast, and a bottom surface that includes a strip of hook and loop fastener material. The sole body has a concave top surface with a complimentary strip of hook and loop fastener material that mates with the hook and loop fastener material on the bandage. The bandage may be integrally molded with the cast, or bonded to the cast after the cast has been set. The present invention is also drawn to the method of attaching the bandage to the cast, and the cast prepared thereby.

Casts are usually made of either plaster or fiberglass. In making a plaster cast, a physician will customarily use a three inch wide bandage roll impregnated with plaster. The bandage is dipped into water, and then applied to the injured leg. When applied to a plaster cast, the present invention takes advantage of the materials and stages of this process. During the plaster casting process, the top surface of the bandage is adhered to the cast while the plaster is still wet. The bandage may also be impregnated with plaster to increase the strength of the bond between the bandage and the cast. When a fiberglass cast is used, an adhesive is applied to the top surface of the bandage, by which the bandage is bonded to the cast.

The hook and loop fastener material on the bandage serves a dual purpose. In addition to serving as a fastener for the sole body, the hook and loop fastener material protects the cast and the surface being walked on, when the sole body is removed. To this end, preferably the loop fastener material is attached to the bandage, while the hook fastener material is attached to the sole body. The loop fastener material is much softer than the hook fastener material, and acts as a protective barrier, keeping the plaster in the cast from cracking, and preventing floors from being scratched by the plaster when the sole body is removed. In addition, the loop fastener material on the bandage will not stick to a surface with small loops, such as a carpet. The hook and loop fasteners provide a quick connection between the cast and the sole body. The patient can later simply peel off the sole body when it is not needed, as when in bed, or to avoid tracking dirt on a carpet that has been picked up by the sole body. To reattach the sole body, the patient simply steps on it with the cast.

Accordingly, it is a principal object of the invention to provide a sole for a walking cast to make it easier for a person with an injured leg to walk.

It is another object of the invention to provide a walking cast with a detachable sole, so that the sole can be removed when it is not needed.

It is a further object of the invention to provide a walking cast with a removably attached sole using hook and loop fasteners in such a way that when the sole is removed, the cast will not accidently be stuck to carpets or other surfaces.

Still another object of the invention is to provide an open-toed walking cast with a removable sole that will accommodate toes extending from the cast.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 3 is a bottom plan view of the bandage used to connect the removable sole to the cast, according to the present invention.

FIG. 4 is a top plan view of the removable sole of the present invention.

Similar reference characters denote corresponding features consistently throughout the attached drawings.

DETAILED DESCRIPTION OF THE PREFERRED EMBODIMENTS

Figure 1:
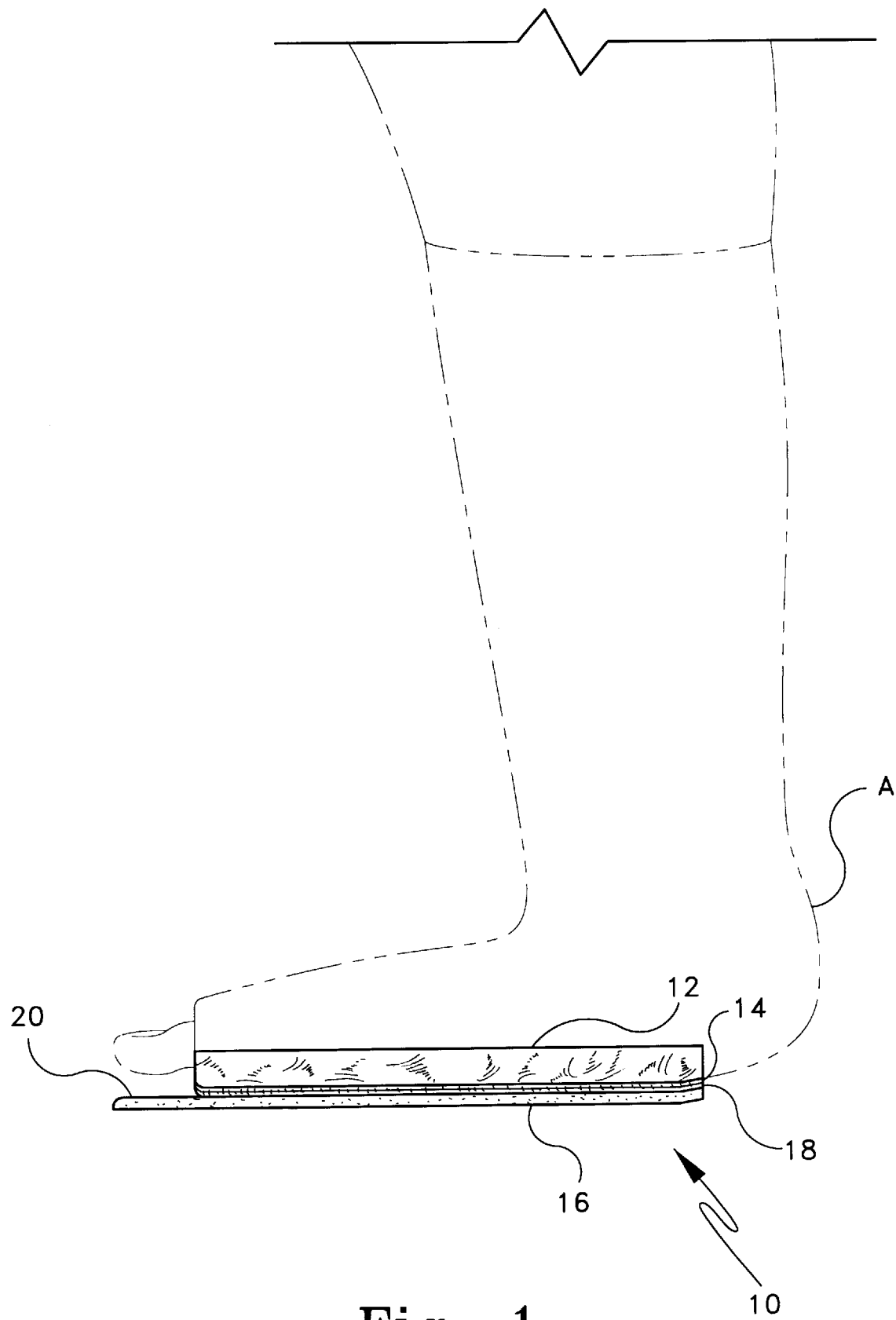
FIG. 1 is an environmental left side elevational view of a cast with a removable sole on the right foot of an injured person, according to the present invention.
Figure 2:
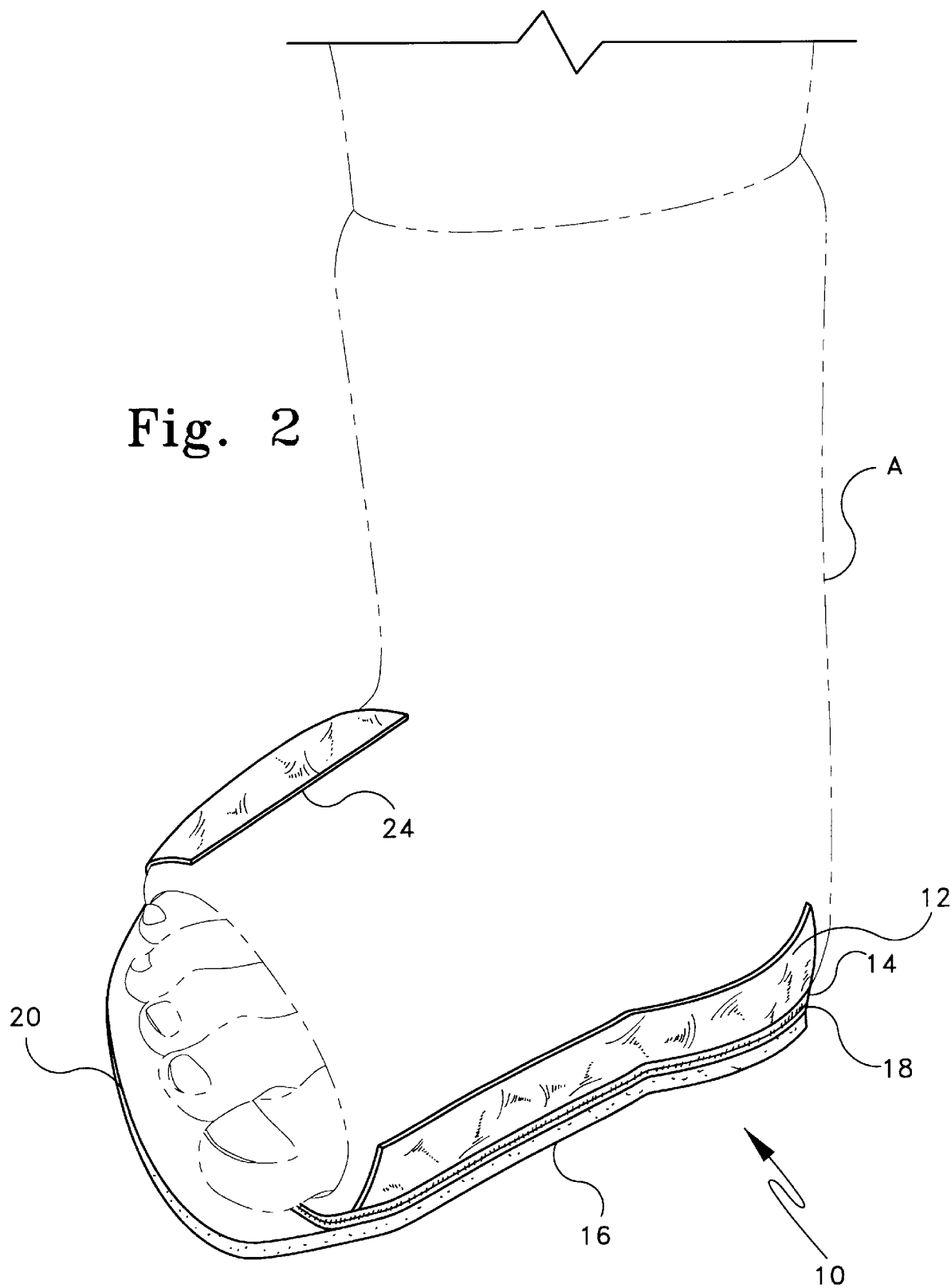
FIG. 2 is an environmental perspective view of the cast with the removable sole of FIG. 1.

The present invention is a removable sole for a walking cast, a walking cast having the removable sole and a method of making the walking cast and the removable sole. FIGS. 1 and 2 show the invention 10 including a cast A on the right foot of an injured person. A bandage 12 is attached to the bottom of the cast. In FIG. 2 it can be seen that the left side 22 and right side 24 of the bandage are bonded to the sides of the cast A. On the bottom of the bandage is a strip of loop fasteners 14. A sole body 16 has a strip of hook fasteners 18 on the top side thereof, which engage the loop fasteners 14 on the bandage, so that the sole body 16 is removably attached. When the cast A is of the opened-toed type, a toe receiving portion 20 on the top of the sole body 16 is left free of the fasteners.

FIG. 3 is a bottom plan view of the bandage 12 of the present invention, showing the strip of loop fasteners 14 attached to the central portion of the bandage 12. The left side 22 and right side 24 of the bandage 12 do not contact the top surface of the sole 16, and therefore are left free of fasteners. The lack of fasteners 14 on the left and right sides 22 and 24, also renders these portions of the bandage 12 more flexible to cover the sides of the cast A for attaching the bandage 12 to the cast A. The bandage 12 is bonded to the cast A using one of two methods, depending on the material of the cast A. When a plaster cast is used, the top surface of the bandage is applied to the cast A while the plaster of the cast A is still wet, thereby forming a plaster bandage (as the bandage becomes saturated with the plaster). Alternatively, when a fiberglass cast is used, the bandage 12 is bonded to the cast A using an adhesive.

In the preferred embodiments, the bandage 12 is made of the same material as the cast A, i.e., a fiberglass fabric with a fiberglass cast and a plaster bandage (preferably presoaked with plaster), for a plaster cast. In either case the strongest bond is achieved when the bandage is formed integrally with the cast during the casting process, and is thereby incorporated directly into the cast. The loop fastener material 14 is attached to the fabric of the bandage by a suitably strong means, (preferably stitching) to avoid separation during use.

FIG. 4 is a top plan view of the sole body 16, showing the strip of hook fastener material 18, and the toe receiving portion 20 on the top of the sole body 16 that is left free of fasteners. The top surface of the sole body 16 is concave to better conform to the shape of the bottom of the cast A. As previously discussed, it is preferable that the loop material of the hook and loop fasteners is attached to the bandage 12 and the hook material is attached to the sole body 16. The loop material on the bottom of the cast A provides a soft surface that does not scratch hard surfaces or become entangled in carpeted surfaces, when the sole body 16 is removed from the cast A. If hook material were used on the bottom of the bandage, the hooks would tend to get entangled on the naturally occurring loops in a carpet or rug. The soles, bandages and walking casts of the present invention are made in a variety of sizes, to fit adults and children with different shoe sizes.

It is to be understood that the present invention is not limited to the embodiments described above, but encompasses any and all embodiments within the scope of the following claims.

I claim:

1. A removable sole for a walking cast, said sole comprising:

a bandage adapted to be permanently attached to the walking cast, said bandage having a top surface for adhering to bottom and side surfaces of the cast, and a bottom surface including a first strip of loop fastener material; and a sole body, said sole body having a top surface with a complementary strip of hook fastener material for engaging said first strip of loop type fastener material on said bandage, and a bottom surface, said top surface of said sole body includes a toe receiving portion, and said complementary strip of hook type fastener material covers all of said top surface except for said toe receiving portion.

2. The removable sole for a walking cast according to claim 1, wherein said first strip of loop type fastener material is sewn to said bottom surface of said bandage.

3. The removable sole for a walking cast according to claim 1, wherein said top surface of said sole body is concave.

4. A walking cast, comprising:

a cast body;

a bandage permanently attached to said cast body, said bandage including a top surface bonded to bottom and side surfaces of said cast body, and a bottom surface including a first strip of hook and loop fastener material, wherein said first strip of hook and loop fastener material is sewn to said bottom surface of said bandage; and a sole body, said sole body having a top surface with a complementary strip of hook and loop fastener material for engaging said first strip of hook and loop fastener material on said bandage, and a bottom surface.

5. The walking cast according to claim 4, wherein:

said first strip of hook and loop fastener material consists of loop fasteners; and said complementary strip of hook and loop fastener material consists of hook fasteners.

6. The walking cast according to claim 5, wherein:

said cast body is an open toed cast;

said top surface of said sole body includes a toe receiving portion; and said complementary strip of hook and loop fastener material covers all of said top surface except for said toe receiving portion.

7. The walking cast according to claim 4, wherein:

said cast body is a plaster cast;

said top surface of said bandage is a plaster bandage; and said plaster bandage and said plaster cast form an integral unit.

8. The walking cast according to claim 4, wherein:

said cast body is a fiberglass cast; and said top surface of said bandage includes an adhesive for bonding said bandage to said fiberglass cast.

9. The sole for a walking cast according to claim 4, wherein said top surface of said sole body is concave.

10. A method of making a walking cast and a removable sole therefor, said method of making comprising the steps of:

attaching a first strip of hook and loop fastener material to a bottom surface of a bandage;

permanently bonding a top surface of the bandage to bottom and side surfaces of the cast;

providing a sole body having a top surface with a complementary strip of hook and loop fastener material, and a bottom surface; and engaging the first strip of hook and loop fastener material with the complementary strip of hook and loop fastener material.

11. The method according to claim 10, said providing step further comprising:

providing the top surface of the sole body with a toe receiving portion; and covering all of the top surface of the sole body except for the toe receiving portion, with the complementary strip of hook and loop fastener material.

12. The method according to claim 10, wherein the cast is a plaster cast and the bandage is a plaster bandage, said bonding step further comprising:

bonding the bandage to the cast by attaching the bandage to the cast while the plaster of the cast and the bandage is wet.

13. The method according to claim 10, wherein the cast is a fiberglass cast and the bandage is made of fiberglass fabric, said bonding step further comprising:

applying an adhesive to the top surface of the bandage; and bonding the bandage to the cast.

14. The method according to claim 10, wherein said attaching step further comprises sewing the first strip of hook and loop fastener material to the bottom surface of the bandage.

* * * * *